(12) United States Patent
Liu

(10) Patent No.: US 8,258,342 B2
(45) Date of Patent: Sep. 4, 2012

(54) PROCESS FOR MAKING A (METH)ACRYLAMIDE MONOMER

(75) Inventor: Leo Zhaoqing Liu, Shanghai (CN)

(73) Assignee: Rhodia Operations (FR)

( * ) Notice: Subject to any disclaimer, the term of this patent is extended or adjusted under 35 U.S.C. 154(b) by 909 days.

(21) Appl. No.: 12/077,384

(22) Filed: Mar. 19, 2008

(65) Prior Publication Data

US 2008/0234515 A1 Sep. 25, 2008

Related U.S. Application Data

(60) Provisional application No. 60/919,734, filed on Mar. 23, 2007.

(51) Int. Cl.
*C07C 231/02* (2006.01)

(52) U.S. Cl. .................. 564/135; 564/204

(58) Field of Classification Search .............. None
See application file for complete search history.

(56) References Cited

U.S. PATENT DOCUMENTS

| | | | |
|---|---|---|---|
| 4,206,143 A | 6/1980 | Wenzel et al. | |
| 4,287,363 A | 9/1981 | McEntire | |
| 4,675,442 A * | 6/1987 | Besecke et al. | 564/135 |
| 4,859,460 A * | 8/1989 | Mahieu et al. | 424/70.2 |
| 2005/0176911 A1 | 8/2005 | Zanini et al. | |
| 2007/0010591 A1 | 1/2007 | Vanneste et al. | |

FOREIGN PATENT DOCUMENTS

| | | |
|---|---|---|
| DE | 2816516 | 4/1978 |
| EP | 0362119 | 7/1993 |

* cited by examiner

*Primary Examiner* — Yevegeny Valenrod

(57) ABSTRACT

A method for making a (meth)acrylamide monomer, comprises reacting a (meth)acrylate ester with an amino-functional compound in an organic solvent in the presence of a transesterification catalyst.

7 Claims, No Drawings ved
PROCESS FOR MAKING A (METH)ACRYLAMIDE MONOMER

This application claims the benefit of U.S. Provisional Application No. 60/919,734, filed Mar. 23, 2007.

FIELD OF THE INVENTION

This invention relates to a process for making a (meth) acrylamide monomer.

BACKGROUND OF THE INVENTION

Production of (meth)acrylamide monomers, such as dimethylaminopropylmethacrylamide ("DMAPMA"), by aminolysis of a (meth)acrylate ester in the presence of a catalyst is known, but competing side reactions produce Michael addition adducts and typically lower the yield of DMAPMA product. The problem of competing side reactions has been addressed by cracking the adduct at high temperature in order to recover DMAPMA, as described in U.S. Pat. No. 4,287,363, or by seeking to reduce the amount of the un-wanted adducts via use of a large excess of (meth)acrylate ester, as described in U.S. Pat. No. 4,206,143 and in DE 2,816,516. Cracking the adduct is tedious and may result in low yield due to the polymerization at the cracking temperature. In the latter process, the need to recover the non-reacted excess ester from the product mixture and the inefficient utilization of the reactor volume result in a very high cost (meth)acrylamide monomer product.

What is needed in the art is a more convenient and/or lower cost route to (meth)acrylamide monomers.

SUMMARY OF THE INVENTION

In a first aspect, the present invention is directed to a method for making a (meth)acrylamide monomer, comprising reacting a (meth)acrylate ester with an amino-functional compound in an organic solvent in the presence of a transesterification catalyst.

DETAILED DESCRIPTION OF INVENTION AND PREFERRED EMBODIMENTS

As used herein, the terminology "($C_x$-$C_y$)" in reference to an organic group, wherein x and y are each integers, indicates that the group may contain from x carbon atoms to y carbon atoms per group.

As used herein, the term "(meth)acrylic" means acrylic, methacrylic or a mixture of acrylic and methacrylic.

As used herein, the term "alkyl" means a monovalent saturated straight chain or branched hydrocarbon group, more typically a monovalent saturated ($C_1$-$C_6$) hydrocarbon group, such as for example, methyl, ethyl, n-propyl, iso-propyl, n-butyl, sec-butyl, t-butyl, pentyl, or n-hexyl.

As used herein, the term "alkylene" means a bivalent saturated straight chain or branched hydrocarbon group, more typically a divalent saturated ($C_1$-$C_6$) hydrocarbon group, such as for example, methylene, dimethylene, trimethylene.

As acknowledged above, it is known to conduct aminolysis of a (meth)acrylic ester using an excess of the ester. We have discovered that the a portion of the ester reactant can be partially replaced with an inert solvent, such as xylene, without sacrificing the reaction time and the yield, thus reduced the amount of reactant. The solvent also provides a higher reaction temperature and, optionally, the ability to reduce the water content of the reaction mixture.

Suitable non-polar organic solvents include organic solvents that are inert or substantially inert under the anticipated reaction conditions and include, aromatic hydrocarbon solvents, for example, xylene, benzene, toluene, linear aliphatic hydrocarbon solvents, such as hexane, decane, undecane, and dodecane, mineral spirits, and cyclic hydrocarbons, such as cyclohexane and cycloheptane.

In one embodiment, the reaction is conducted in from about 1 to about 200 parts by weight ("pbw"), more typically, from about 10 to about 100 pbw, organic solvent per 100 pbw of the total charge of (meth)acrylic ester.

In one embodiment, the reaction is conducted using a total amount of from about 0.1 up to but not including 1.0 mole, more typically, from about 0.25 to about 0.75 mole, of amine compound per mole of (meth)acrylic ester compound.

The reactants may each be introduced to the reaction mixture as one or more discrete portions or as a feed into the reaction mixture over the course of the reaction, or as a combination thereof, for example, as an initial shot of a first portion followed by a feed of the remaining portion.

In one embodiment, the entire charge of (meth)acrylic ester compound is mixed with the organic solvent prior to addition of the amine compound and the charge of amine compound is then fed into the mixture over time, typically over a period of from about 1 to about 5 hours, more typically over a period of from about 2 to about 4 hours. It is believed that maintaining the low ratio of amine compound to (meth)acrylic ester discourages undesired side reactions, such a Michael addition. However, prolonged reaction time will increase the process time and potentially allow undesired polymerization of contents of the reaction mixture to occur.

Suitable transesterification catalysts are know in the art and include, for example, organotin, organoziconium, and organotitanium compounds, such as dialkyltin oxides, dialkyl-dialkoxytin compounds, tetramethoxytin compounds, bis(di-alkylamino)-dialkyltin compounds, and tetraalkyltitanate compounds, such as tetraisobutyltitanate, as well as mixtures of such catalysts. Typically, the catalyst is a dialkyltin oxide catalyst, more typically dibutyltin oxide, and/or dioctyltin oxide.

In one embodiment, the reaction mixture comprises from about 0.01 to about 10 percent by weight ("wt %"), more typically from about 1 to about 5 wt %, of the transesterification catalyst.

In one embodiment, the transesterification reaction is conducted within a temperature range of from about 10° C. to about 150° C., more typically from about 50° C. to about 120° C. Typically the reaction is run for a reaction time of from about 2 to about 10 hours, more typically from about 4 to about 6 hours.

In one embodiment, the reaction mixture for making the (meth)acrylamide monomer further comprises a polymerization inhibitor, such as hydroquinone compounds, phenothiazine, or a mixture thereof, to inhibit polymerization of the (meth)acrylic ester reactant and/or the product monomer during synthesis of the amino(meth)acrylamide monomer. Suitable hydroquinone compounds include, for example, such as hydroquinone and methylhydroquinone.

In one embodiment, the reaction for making the (meth) acrylamide monomer is conducted with an air sparge to inhibit polymerization of the (meth)acrylic ester reactant and/ or the product monomer during synthesis of the amino(meth) acrylamide monomer.

In one embodiment, a (meth)acrylamide monomer is made according to Scheme A:

Scheme A $$H_2C=\underset{R^1}{C}-\underset{\underset{O}{\|}}{C}-O-R_2 \quad + \quad H_2N-R^3$$

(I) (II)

↓ catalyst, solvent

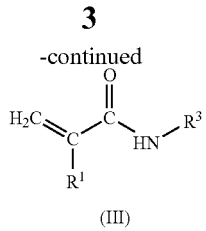

(III)

by reacting one or more (meth)acrylic esters according to structure (I), wherein: $R^1$ is H or $(C_1-C_4)$alkyl, and $R^2$ is an aliphatic or aromatic hydrocarbon group, more typically $(C_1-C_4)$alkyl, with one or more amino-functional compounds according to structure (II), wherein $R^3$ is an organic group that is substantially inert under the reaction conditions, in an organic solvent and in the presence of a transesterification catalyst to make a (meth)acrylamide monomer according to structure (III).

In one embodiment compound (II) is a dialkylaminoalkylamine compound according to structure (II-a):

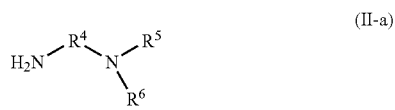

(II-a)

wherein
$R^4$ is a divalent linking group, typically $(C_1-C_6)$alkylene which may optionally be substituted on one or more carbon atoms or interrupted at one or more points by a heteroatoms, more typically, $(C_1-C_6)$alkylene, and $R^5$ and $R^6$ are each independently alkyl, more typically $(C_1-C_6)$alkyl, or may be fused to form, with the nitrogen atom to which they are attached, a saturated or unsaturated heterocyclic ring structure, which may optionally comprise additional ring member nitrogen atoms and which may optionally substituted on one or more of the ring atoms with alkyl or oxygen.

In the case that compound (II) is a dialkylaminoalkylamine compound according to structure (II-a), the (meth)acrylamide monomer is a compound according to structure (III-a):

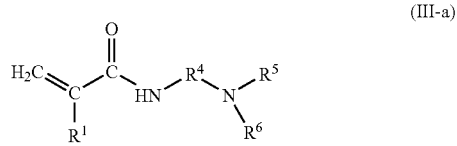

(III-a)

wherein $R^1$, $R^4$, $R^5$, and $R^6$ are each as defined above.

In one embodiment, $R^5$ and $R^6$ are fused to form a saturated or unsaturated monocyclic heterocyclic ring structure which may optionally comprise additional ring member nitrogen atoms, such as, for example, pyrrolidinyl, pyrrolinyl, pyrrolyl, imidazolidinyl, imidazolyl, pyrazolidinyl, piperidinyl, piperazyinyl, pyrazolyl, pyridinyl, pyrazinyl, pyrimidinyl, or pyridazinyl group, In one embodiment, $R^5$ and $R^6$ are fused to form a saturated or unsaturated monocyclic heterocyclic ring structure which may optionally comprise additional ring member nitrogen atoms, that is substituted on one or more of the ring atoms with alkyl or oxygen, such as, for example, for example, 1-(2-Aminoethyl)-2-imidazolidinone.

In one embodiment, a product mixture of a (meth)acrylamide monomer (III) and one or more (meth)acrylate co-products (V) is made according to Scheme B:

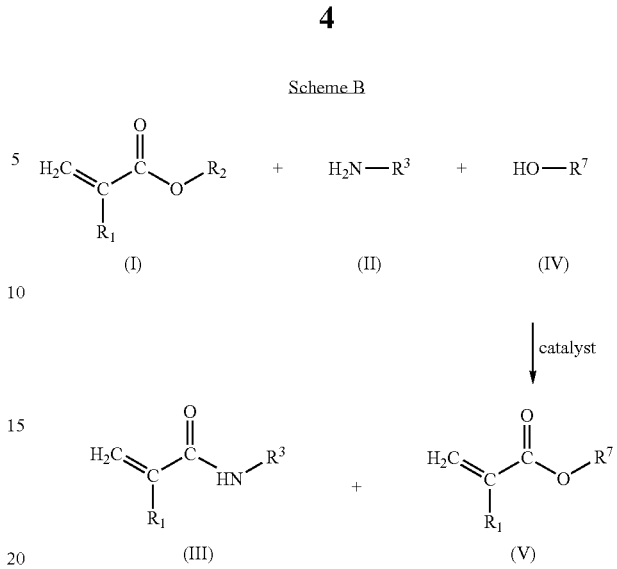

by reacting a (meth)acrylic ester (I) with a mixture of an amino-functional compound (II) and an alcohol (V), wherein $R^1$, $R^2$, and $R^3$ are each as described above and $R^7$ is an organic group that is substantially inert under the reaction conditions. Typically $R^7$ is $(C_1-C_{20})$alkyl and typically $R^7 \neq R^2$.

The alcohol compound (IV) and co-product (V) each serve as solvents for the reaction of (meth)acrylate ester (I) and amino-functional compound (II), and serve to lower the ratio of aminofunctional compound (II) to (meth)acrylate ester (I), thus discouraging the formation of the unwanted Michel addition by-product of amino-functional compound (II).

The amino-functional compound (II) and alcohol (IV) are selected in order to provide a (meth)acrylate co-product (V) that is easily separable from the (meth)acrylamide monomer product (III). In one embodiment, the amino compounds (II) and alcohol (IV) are selected to provide a (meth)acrylamide monomer product (III) and (meth)acrylate co-product (IV) having boiling points that are sufficiently different, for example, by greater than or equal to 10° C., more typically by greater than or equal to 20° C., as to be readily separable by distillation. In one embodiment, $R^7 = R^3$.

The reaction mixture may include any ratio of amino-functional compound (II): alcohol (IV) In one embodiment, the total amount of amino-functional compound (II) comprises greater than or equal to about 10 mole %, more typically greater than or equal to about 60 mole % of the amount of alcohol compound (IV).

In one embodiment, a product mixture of a (meth)acrylamide monomer (III-a) and one or more (meth)acrylate co-products (V-a) is made according to Scheme B-1:

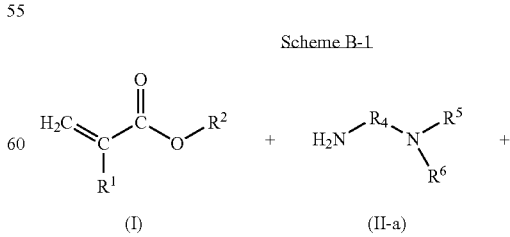

-continued

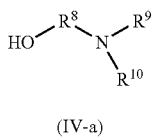

(IV-a)

↓ catalyst solvent

-continued

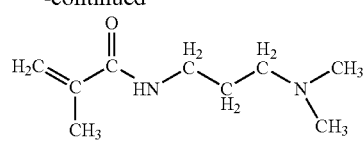

(III-1)

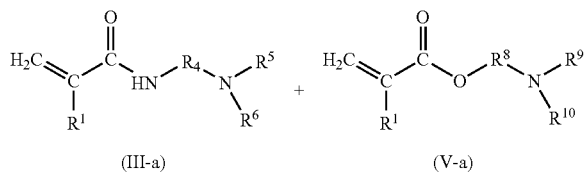

by reacting a (meth)acrylic ester (I) with a mixture of an amino-functional compound (II-a) and an alcohol (IV-a), wherein:

$R^1$, $R^2$, $R^4$, $R^5$, and $R^6$ are each as described above, $R^8$ is a divalent linking group, typically ($C_1$-$C_6$)alkylene which may optionally be substituted on one or more carbon atoms or interrupted at one or more points by a heteroatoms, $R^9$ and $R^{10}$ are each independently alkyl, more typically ($C_1$-$C_6$)alkyl, or may be fused to form, with the nitrogen atom to which they are attached, a saturated or unsaturated heterocyclic ring structure, which may optionally comprise additional ring member nitrogen atoms and which may optionally substituted on one or more of the ring atoms with alkyl or oxygen.

In one embodiment, a mixture of transesterified products is made by conducting a reaction according to Scheme B-1, wherein $R^1$ is H or methyl, and $R^2$ is methyl, $R^4$ and $R^8$ are each independently ($C_1$-$C_6$)alkylene $R^5$, $R^6$, $R^9$, and $R^{10}$ are each independently ($C_1$-$C_6$)alkyl.

In one embodiment, $R^9$=$R^5$, and $R^{10}$=$R^6$.

EXAMPLES 1-5

In the processes of Examples 1 to 5, a methacrylamide monomer (III-1) was made according to Scheme A-1:

Scheme A-1

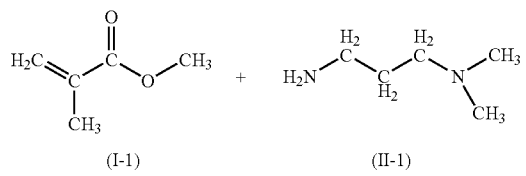

↓ catalyst solvent by reacting a methacrylic ester (I-1) with a amine compound (II-1) in a solvent and in the presence of a transesterification catalyst, as described below. For each of Examples 1-5, material charges are listed below in TABLE I—Part A and results are listed below in TABLE I—Part B.

In the process of Example 1, to a 500 ml flask, equipped with a thermometer, gas inlet, addition port, magnetic stirrer and distillation column of 5-plates topped with a distillation head connecting to a condenser, were charged xylene 20 g, methyl methacrylate (MMA, Aldrich) 62.7 g and phenothiazine (PTZ) 0.31 g. The mixture was heated toward to reflux with a very slow dry air purge. When the batch temperature reached 70° C., dibutyltin oxide ($Bu_2SnO$, Eurecat 9555 from Crompton) 2.81 g was added. Heating was continued. When the batch began to boil at 103° C., dimethylaminopropylamine (DMAPA from BASF) 8.0 g was added quickly. Distillate started to come out after 20 minutes and within 30 minutes the batch became free from insoluble catalyst and clear. Then, 33.0 g DMAPA was added over 3 hours and the batch temperature was allowed to rise to 140° C. Distillate was collected. After the addition, the batch was held at 140-150° C. for two hours. A total 20 grams of methanol/methacrylate azeotrope was collected. Note that little distillate was collected 30 minutes after DMAPA addition, indicating the reaction was almost done. The remaining methyl methacrylate and xylene was distillated in vacuum until the batch temperature decreased to 135° C. at −17.5 inch Hg. A total 29 g of the distillate was collected, which could be recycled, and 74.2 gram residual was left in the reactor. HPLC analysis showed 89.7% DMAPMA and 2.0% methacrylic acid. This accounted for 97.4% yield from DMAPA (Ex #1, Table 1).

The process of Example 2 was run according to that described above for the process of Example 1, except that DMAPA was fed less evenly, and rate fluctuation was allowed. Similar yield to Example 1 was obtained.

The process of Example 3 was run according to that described above for the process of Example 1, except no solvent was used. A slightly lower yield was obtained.

The process of Example 4 was run according to that described above for the process of Example 1, except a mixture of hexane and xylene was used as solvent. Addition of DMAPA was done over 2 hours and hexane was distilled out during the early stage of reaction. Similar yield to Example 1 was obtained.

The process of Example 5 was run according to that described above for the process of Example 1, except more xylene as solvent and less dibutyl tin oxide catalyst were used. Addition of DMAPA was done over 1.5 hours. Similar yield to Example 1 was obtained.

EXAMPLES 6-11

In the processes of Examples 6 to 11, a methacrylamide monomer (III-a-1) was made according to Scheme B-2:

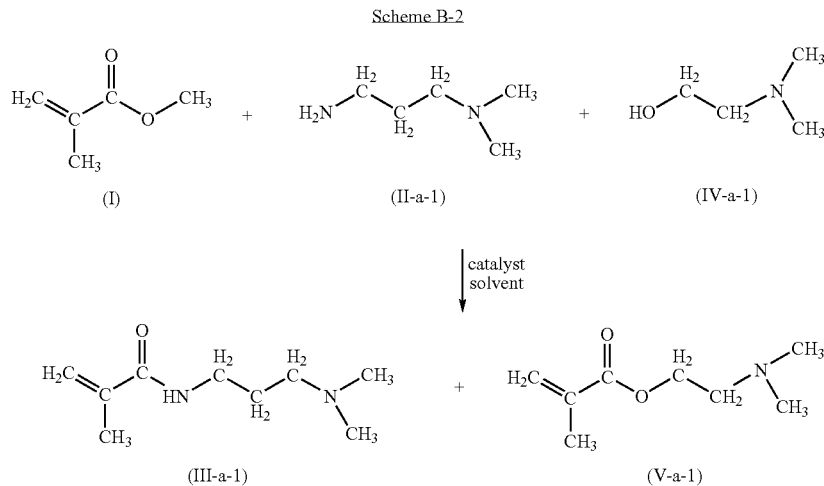

by reacting a methacrylic ester (I-1) with an amine compound (II-a-1) in an alcohol compound (IV-a-1) as a solvent and in the presence of a transesterification catalyst, as described below. For each of Examples 6-11, material charges are listed below in TABLE I—Part A and results are listed below in TABLE I—Part B.

In the process of Example 6, to a 500 ml flask, equipped with thermometer, gas inlet, addition port, magnetic stirrer and distillation column of 5-plates topped with a distillation head connecting to a condenser, were charged methyl methacrylate (Aldrich) 206.7 g and phenothiazine 0.3 g. The mixture was heated toward to reflux with a very slow dry air purge. When batch temperature reached 70° C., dibutyltin oxide (Eurecat 9555 from Crompton) 5.01 g was added. Heating continued. When the batch began to boil at 101° C., dimethylethanolamine (DMEA from BASF) 11.8 g was added quickly. Distillate started to come out after 15 minutes and the batch became free from insoluble catalyst and clear. Then, 35.3 g DMEA was added over 45 minutes and the batch temperature was allowed to rise. Distillate was collected. After finishing DMEA, Tyzor TPT 0.35 g was added, the batch was held at reflux at 103-107° C. for one hour then DMAPA 53.34 g was added over 90 minutes. Continue to collect distillate at 60-65° C. and to allow the reaction temperature to rise. After the addition, the batch was held at 120-150° C. for three hours. The batch temperature rose gradually. A total 57 grams of methanol/methacrylate azeotrope was collected. The remaining methyl methacrylate was distilled under vacuum until the batch temperature decreased to 130° C. at −17.5 inch Hg. A total 63.5 g of the distillate was collected, which would be recycled. HPLC analysis showed 185 gram residual contained 45.4% DMAPMA, 41.9% dimethylaminoethyl methacrylate (DMAEMA) and 1.6% methacrylic acid. This accounted for 95% yield for DMAPMA from DMAPA and 94% for DMAEMA from DMEA (Ex #6).

The process of Example 7 was run according to that described above for the process of Example 6, except that dibutyltin oxide from Aldrich was used as the transesterification catalyst.

The process of Example 8 was run according to that described above for the process of Example 6, except that dioctyltin oxide (Eurecat DOTO, Crompton) was used as the transesterification catalyst.

The process of Example 9 was run according to the process of Example 7, except that part of the MMA was recycled from previous reactions.

The process of Example 10 was run according to that described above for the process of Example 7, except that small amount of hexane was used to remove any residual amount of water from the system. A lightly better yield was observed.

The process of Example 11 was run according to that described above for the process of Example 6.

TABLE I

Part A

| EX# | Hexane | Xylene | MMA | PTZ/MEHQ | CAT | TPT | DMAPA | DMEA |
|---|---|---|---|---|---|---|---|---|
| 1 | 0 | 20.0 | 62.7 | 0.31/0 | 2.81 | 0 | 41.0 | 0 |
| 2 | 0 | 20.0 | 60.0 | 0.31/0 | 2.80 | 0 | 40.9 | 0 |
| 3 | 0 | 0 | 80.1 | 0.32/0 | 2.80 | 0 | 40.9 | 0 |
| 4 | 27 | 75.2 | 101.2 | 0.30/0 | 3.45 | 0 | 51.8 | 0 |
| 5 | 0 | 96.3 | 95.7 | 0.10/0.097 | 2.86 | 0.60 | 48.8 | 0 |
| 6 | 0 | 0 | 206.7 | 0.30/0 | 5.01 | 0.35 | 53.3 | 47.1 |
| 7 | 0 | 0 | 200.0 | 0.25/0 | 4.67 | 0.35 | 57.48 | 44.60 |
| 8 | 0 | 0 | 200 | 0.25/0.16 | 3.50 | 0 | 54.6 | 44.48 |
| 9 | 0 | 0 | 200 | 0.40/0 | 3.11 | 0.20 | 51.0 | 47.0 |
| 10 | 10.4 | 0 | 201.7 | 0.25/0.16 | 5.05 | 0.30 | 51.00 | 47.30 |
| 11 | 0 | 0 | 119.7 | 0.14/0.11 | 3.02 | 0.25 | 31.0 | 27.7 |

TABLE I-continued

Part B

| EX# | Discharge <90° C. | Discharge >90° C. | Yield DMAPMA (%) HPLC | Yield DMAPMA (%) dist | Yield DMAEMA (%) HPLC | Yield DMAEMA (%) Dist | MMA (%) |
|---|---|---|---|---|---|---|---|
| 1 | 19.6 | 28.9 | 97.4 | — | — | — | 2.0 |
| 2 | 16.5 | 27.3 | 96.9 | — | — | — | 2.3 |
| 3 | 18.8 | 24.1 | 95.2 | — | — | — | 2.6 |
| 4 | 61.1 | 77.0 | 96.9 | 97.4 | — | — | 1.7 |
| 5 | 43.5 | 113.0 | — | 93.0 | — | — | — |
| 6 | 57.3 | 63.5 | 94.9 | — | 93.6 | — | 1.6 |
| 7 | 73.7 | 39.0 | 90.0 | — | — | 87.3 | 1.5 |
| 8 | 60.0 | 51.0 | — | 84.4 | — | 86.1 | 0.1 |
| 9 | 59.3 | 55.5 | — | 100 | — | 82.5 | <0.6 |
| 10 | 42.0 | 75.6 | — | 99.6 | — | 92.3 | 1.5 |
| 11 | 19.6 | 47.7 | — | 99.2 | — | 87.0 | — |

EXAMPLE 12

DMAPMA distillate from the above reactions, containing water-insoluble organotin catalysts and 1300 ppm methacrylic acid (MMA) 170.0 g was mixed with 25% NaOH 2 g and phenothiazine 0.05 g. The mixture was subjected to vacuum distillation. The distillate was collected at 91-93° C. and −30.3 inch Hg to yield 105 g pure DMAPMA (91% yield) containing no water-insoluble and non-detectable MAA (<10 ppm) by HPLC analysis.

The invention claimed is:

1. A method for making a (meth)acrylamide monomer, comprising reacting a (meth)acrylic ester (I) with a mixture of an amino-functional compound (II-a) and an alcohol (IV-a) according to Scheme B-1 in an organic solvent comprising alcohol (IV-a) and in the presence of a transesterification catalyst a product mixture of a (meth)acrylamide monomer (III-a) and one or more (meth)acrylate co-products (V-a):

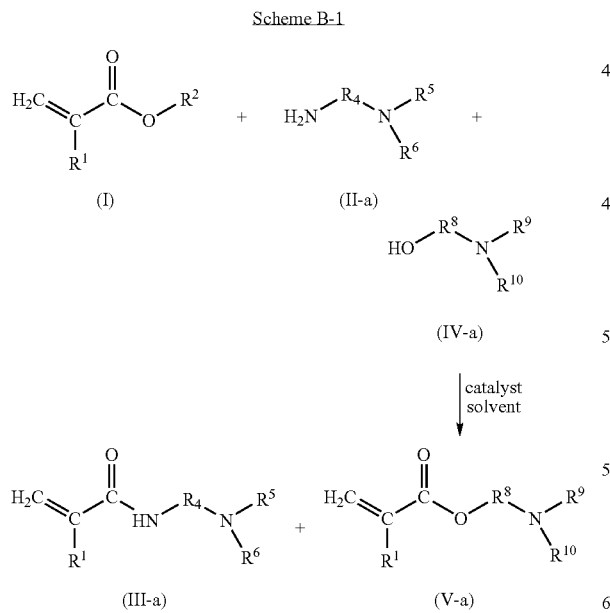

Scheme B-1 wherein:
$R^1$ is H or methyl,
$R^2$ is an aliphatic or aromatic hydrocarbon group
$R^4$ is a divalent linking group, which may optionally be substituted on one or more carbon atoms or interrupted at one or more points by a heteroatoms,
$R^5$ and $R^6$ are each independently alkyl or may be fused to form, with the nitrogen atom to which they are attached, a saturated or unsaturated heterocyclic ring structure, which may optionally comprise additional ring member nitrogen atoms and which may optionally substituted on one or more of the ring atoms with alkyl or oxygen,
$R^8$ is a divalent linking group, typically $(C_1-C_6)$alkylene which may optionally be substituted on one or more carbon atoms or interrupted at one or more points by a heteroatoms, and
$R^9$ and $R^{10}$ are each independently alkyl, or may be fused to form, with the nitrogen atom to which they are attached, a saturated or unsaturated heterocyclic ring structure, which may optionally comprise additional ring member nitrogen atoms and which may optionally substituted on one or more of the ring atoms with alkyl or oxygen.

2. A method for making a (meth)acrylamide monomer, comprising reacting a (meth)acrylic ester (I) with a mixture of an amino-functional compound (II-a) and an alcohol (IV-a) according to Scheme B-1 in an organic solvent comprising alcohol (IV-a) and in the presence of a transesterification catalyst to form a product mixture of a (meth)acrylamide monomer (III-a) and one or more (meth)acrylate co-products (V-a):

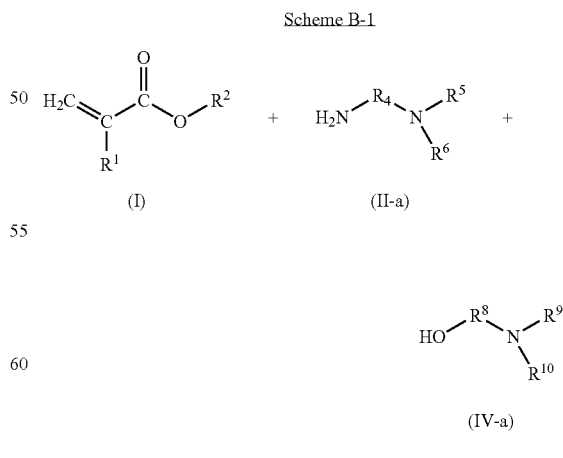

Scheme B-1

-continued

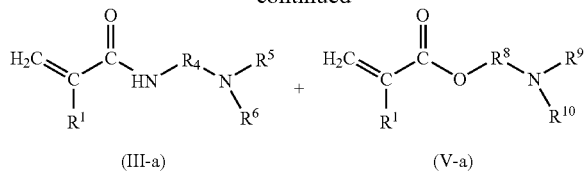

wherein:
R$^1$ is H or methyl,
R$^2$ is methyl,

R$^4$ and R$^8$ each independently (C$_1$-C$_6$)alkylene, and
R$^5$, R$^6$, R$^9$, and R$^{10}$ are each independently (C$_1$-C$_6$)alkyl.

3. The method of claim 2, wherein R$^9$=R$^5$ and R$^{10}$=R$^6$.

4. A method for making a (meth)acrylamide monomer, comprising reacting a methacrylate ester (I) with a mixture of an amino-functional compound (I-a-1) and an alcohol (IV-a-1) according to Scheme B-2 in an organic solvent comprising alcohol (IV-a-1) and in the presence of a transesterification catalyst to form a product mixture of a methacrylamide monomer (III-a-1) and a methacrylate co-product (V-a-1):

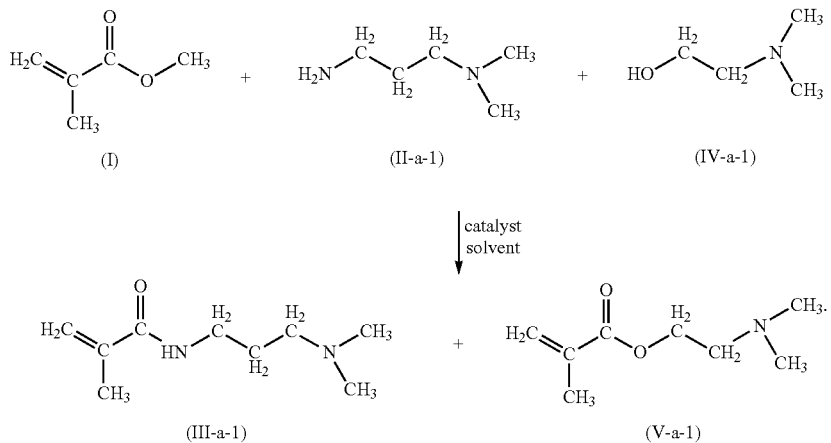

5. The method of claim 1, wherein the organic solvent further comprises an organic solvent selected from aromatic hydrocarbon solvents, linear aliphatic hydrocarbon solvents, and cyclic hydrocarbons.

6. The method of claim 2, wherein the organic solvent further comprises an organic solvent selected from aromatic hydrocarbon solvents, linear aliphatic hydrocarbon solvents, and cyclic hydrocarbons.

7. The method of claim 4, wherein the organic solvent further comprises an organic solvent selected from aromatic hydrocarbon solvents, linear aliphatic hydrocarbon solvents, and cyclic hydrocarbons.

* * * * *